United States Patent
Soyer et al.

(10) Patent No.: US 6,207,628 B1
(45) Date of Patent: *Mar. 27, 2001

(54) AQUEOUS SOLUTION

(75) Inventors: Patrice Soyer, Guignes; Arila Pochet, Gretz, both of (FR)

(73) Assignee: Essilor International Compagnie Generale d'Optique, Charenton Cedex (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/072,790

(22) Filed: May 5, 1998

(30) Foreign Application Priority Data

May 5, 1997 (FR) .................................................. 97 05489

(51) Int. Cl.[7] ................................. C11D 3/22; C11D 7/26; A61L 2/18
(52) U.S. Cl. ........................... 510/112; 510/421; 510/470; 510/471; 510/475; 510/504
(58) Field of Search ..................................... 510/112, 421, 510/470, 471, 504, 475

(56) References Cited

U.S. PATENT DOCUMENTS

| 4,259,202 | 3/1981 | Tanaka et al. .................. 252/107 |
|---|---|---|
| 4,450,090 | * 5/1984 | Kinney . |
| 4,690,818 | * 9/1987 | Puchalski, Jr. et al. . |
| 5,705,532 | * 1/1998 | Modak et al. . |
| 5,853,767 | * 12/1998 | Melman . |

FOREIGN PATENT DOCUMENTS

| 0079030 | 11/1982 | (EP) . |
|---|---|---|
| WO 95/00615 | 1/1995 | (WO) . |
| WO 95/00616 | 1/1995 | (WO) . |
| WO 95/08352 | 3/1995 | (WO) . |

OTHER PUBLICATIONS

Polovsky et al., PEG–120 Methyl Glucoside Dioleate A New Agent for Viscosity Enhancement in the Field of Shampoos, Liquid Soap, and other Detergent SystemsComun. Jorn. Com. Esp Deterg 14th, 83–102, Sep. 16, 1999, 1983.*

Polovsky et al., "A New agent for Viscosity Enhancement in the Field of Shampoos, Liquid Soaps, and other Detergent Systems," Comun. JOrn>Com. Esp. Deterg. (1983), 14th, 83–102, 1983.*

Grant& Hackh's Chemical Distionary, 5th edition p. 98, 1987.*

* cited by examiner

*Primary Examiner*—Margaret Einsmann
(74) *Attorney, Agent, or Firm*—Fulbright & Jaworski LLP

(57) ABSTRACT

The aqueous maintenance solution according to the invention is characterized by the presence of an effective amount of polyethylene glycol 120 methylglucose dioleate. Application: to aqueous maintenance solutions for hard contact lenses.

60 Claims, No Drawings

AQUEOUS SOLUTION

The present invention relates generally to an aqueous solution for maintaining contact lenses, in particular hard contact lenses.

Aqueous solutions for maintaining contact lenses generally have the function of decontaminating and cleaning the lenses.

To be effective, these solutions need to have a combination of several properties.

Firstly, they need to ensure effective decontamination of the lenses for a broad spectrum of microorganisms, and effective cleaning of the surfaces of the lenses, without their active principles being absorbed by the lenses.

Moreover, in order to simplify the maintenance of lenses, it is desirable for them to be re-usable directly after soaking in the maintenance solution, i.e. without it being necessary to carry out one or more rinses with water. In this case, it is particularly important, since the maintenance solution must remain in contact with the user's eye, that this solution is not irritant, is well tolerated and leaves the lenses comfortable to wear throughout the period of continuous use, generally a day.

An important factor for the comfort of use of treated lenses is the viscosity of the maintenance solution. This viscosity should not be too low or too high. If the viscosity of the solution is too low, the solution will not wet the surfaces of the lens correctly; the user will perceive the lens as a foreign body in the eye, and if the viscosity is too high, the solution can give rise to cloudy vision and lead to a greasy feel on the lens, which users find uncomfortable.

Another important factor for the comfort of use of lenses treated with a maintenance solution is the ability of the maintenance solution to retain a relatively large amount of water on the surfaces of the lens treated, such that the surfaces of the lens are humidified throughout a prolonged period and the wettability of the surfaces of the lens is retained. This characteristic, which will be denoted hereinbelow as "the humidity-retaining ability" is an important factor for the user's comfort. This humidity-retaining ability is a particularly important factor in the case of hard contact lenses, which generally have a low ability to retain water on their surfaces.

In order to improve the wettability of contact lens surfaces, in particular for hard lenses, it has been proposed to incorporate hydrophilic monomers into the maintenance solutions. However, these hydrophilic monomers generally have the drawback of affecting the other physical properties of the lenses.

To solve this problem it has also been proposed to incorporate wetting polymers into the maintenance solutions, but the action of these polymers is weak and disappears rapidly.

To overcome the abovementioned drawbacks, document WO 95/00616 proposes adding to the maintenance solutions a water-soluble poly(ethylene oxide) which is a star polymer containing a hydrophobic core having at least three carbon atoms and at least three hydrophilic poly(ethylene oxide) chains (arms) attached to the core. In addition, the star polymers in document WO 95/00616 must not contain hydrophobic arms attached to the core.

In a preferred embodiment of document WO 95/00616, a second surfactant polymer component, a cationic cellulose polymer, is added to the maintenance solution. This cationic component complexes with the poly(ethylene oxide) star polymer and the complex formed is strongly adsorbed onto the surface of the lenses.

Although the maintenance solutions of document WO 95/00616 are satisfactory, it would be desirable to have available maintenance solutions which afford the contact lens wearer even better comfort.

The object of the present invention is thus to provide a maintenance solution for contact lenses, in particular for hard contact lenses, which overcomes the abovementioned drawbacks.

The subject of the present invention is, more particularly, a maintenance solution as defined above, which gives treated lenses improved humidity-retaining ability.

The subject of the present invention is also a maintenance solution as defined above, which is easy to use, in particular which allows treated lenses to be used directly, i.e. without rinsing, and makes the treated lenses comfortable for the user to wear.

The aims listed above are achieved, according to the present invention, by providing an aqueous maintenance solution for contact lenses, in particular hard contact lenses, characterized in that it comprises an effective amount of polyethylene glycol 120 methylglucose dioleate of formula:

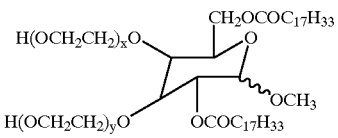

in which x+y=120.

The incorporation of polyethylene glycol 120 methylglucose dioleate into the maintenance solution not only increases the wettability of the lenses by the maintenance solution but also appreciably improves the humidity-retaining ability of the treated lenses. In addition, the maintenance solutions according to the invention make the treated lenses particularly comfortable for the user.

Preferably, the amount of polyethylene glycol 120 methylglucose dioleate present in the solution is between 0.05 and 5% by weight, better still between 0.1 and 2% by weight, relative to the total weight of the aqueous maintenance solution.

As is well known, the aqueous maintenance compositions according to the invention comprise a decontaminating agent. This decontaminating agent, generally an antimicrobial agent, is well known in the art and can consist of a single compound or a mixture of several compounds. Compounds which are useful as decontaminating agents can be any known compounds which are useful as decontaminating agents in aqueous maintenance solutions for contact lenses.

Among these compounds, mention may be made of chlorhexidine (1,1'-hexamethylenebis[5-(p-chlorophenyl) biguanide]) or water-soluble salts thereof, such as chlorhexidine gluconate; polyhexamethylene biguanide (a hexamethylene biguanide polymer also known under the name polyaminopropyl biguanide) or water-soluble salts thereof, such as polyhexamethylene biguanide hydrochloride sold under the trade name Cosmocil CQ® (ICI Americas Inc.); alkylammonium halides, in particular alkyltrimethylammmonium bromides such as tetradecyltrimethylammonium bromide, dodecyltrimethyl-ammonium bromide, hexadecyltrimethylammonium bromide (cetrimonium bromide) sometimes known as "Cetrimide"; benzalkonium halides such as benzalkonium chloride; polymeric quaternary ammonium salts; and mixtures of these compounds.

The recommended decontaminating agents according to the invention are polyaminopropyl biguanide and the water-soluble salts thereof, in particular the product sold under the brand name Cosmocil CQ®, and alkylammonium bromides, in particular cetrimonium bromide, and mixtures thereof.

A decontaminating agent which is particularly preferred according to the invention is a mixture of polyhexamethylene biguanide hydrochloride (Cosmocil CQ®) and cetrimonium bromide.

The amount of decontaminating agent in the maintenance solution according to the invention is an effective amount, i.e. an amount sufficient to decontaminate lenses. In general, the amount of decontaminating agent present in the maintenance solution according to the invention is from $10^{-6}$ to 5% by weight, preferably 0.01 to 0.05% by weight, relative to the total weight of the maintenance solution.

Preferably, the maintenance solutions according to the invention contain an effective amount of one or more nonionic surfactants. Among these nonionic surfactants, mention may be made of fatty acid esters of polyethylene glycol, for example of coconut oil, polysorbates, polyoxyethylene ethers and polyoxypropylene ethers of higher alkanes ($C_{12}$–$C_{18}$). Examples of the above nonionic surfactants comprise polysorbate 20 (sold under the brand name Tween 20®), polyoxyethylene lauryl ether (Brij® 35), polyoxyethylene (40) stearate (Myrj® 52), polyoxyethylene (25) propylene glycol stearate (Atlas® G 2612).

A particularly recommended class of nonionic surfactants comprises poly(oxypropylene)-poly(oxyethylene) adducts of ethylenediamine and poly(oxyethylene)-poly(oxypropylene) block polymers.

The preferred nonionic surfactants are poly(oxyethylene)-poly(oxypropylene) block polymers.

The maintenance solutions according to the invention generally contain from 0.01 to 15% by weight of nonionic surfactant relative to the total weight of the composition, preferably from 0.05 to 1% by weight.

Preferably also, the recommended poly(oxyethylene)-poly(oxypropylene) block polymer nonionic surfactant is present in the maintenance solution in an amount such that the weight ratio between this recommended nonionic surfactant and the polyethylene glycol 120 methylglucose dioleate is about 1:2.

Although this is not preferred, the maintenance solution can also comprise cationic and/or amphoteric surfactants conventionally used in maintenance compositions for contact lenses, in the usual proportions.

The maintenance solutions according to the invention preferably also comprise one or more standard agents for modifying the viscosity. These viscosity-modifying agents are well known and comprise water-soluble cellulose polymers such as hydroxyethyl- or hydroxypropyl cellulose, carboxymethyl cellulose, polyvinylpyrrolidone and poly(acrylic acids). The preferred viscosity-modifying agents are cellulose polymers and in particular hydroxyethyl cellulose.

The viscosity-modifying agent is used in the usual amounts, generally from 0.01 to 4.0% by weight, or less, relative to the total weight of the solution.

Besides the polyethylene glycol 120 methylglucose dioleate, the maintenance solutions according to the invention generally contain other wetting agents conventionally used in maintenance solutions for contact lenses, such as poly(oxyethylene) glycols. These wetting agents are generally present in a proportion of from 0.5 to 5%, preferably 1 to 2% by weight relative to the total weight of the solution.

Preferably also, the wetting agent of poly(oxyethylene) glycol type is present in the maintenance solution in an amount such that the weight ratio between this recommended wetting agent and the polyethylene glycol 120 methylglucose dioleate is about 1:1.

In general, the maintenance solutions according to the invention comprise one or more sequestering agents (or chelating agents), in particular for sequestering calcium and magnesium ions, in an amount which can be up to about 2% by weight relative to the total weight of the solution. Among the sequestering agents which can be used in the solutions of the invention, mention may be made of ethylenediaminetetraacetic acid (EDTA) and its salts, in particular its sodium salt, polyphosphate complexes such as sodium hexametaphosphate, sodium pyrophosphate and sodium tripolyphosphate, gluconic acid, citric acid and tartaric acid and their salts, in particular their sodium salts. The preferred sequestering agent is the sodium salt of EDTA.

The maintenance solutions of the invention also generally contain a buffer. Among the buffers which can be used in the maintenance solution according to the invention, mention may be made of phosphates such as $Na_2HPO_4$, $NaH_2PO_4$ and $KH_2PO_4$, borate buffers such as boric acid, sodium borate, potassium tetraborate or potassium metaborate, or mixtures of these buffers. A recommended buffer is a mixture of monosodium phosphate and disodium phosphate. The amount of buffer used is generally between 0.05 and 2.5% by weight, preferably between 1 and 2% by weight, relative to the total weight of the solution.

Generally, the tonicity of the aqueous maintenance solutions according to the invention is adjusted by adding a standard tonicity agent, such as sodium chloride or a glycerol solution. The preferred tonicity agent is sodium chloride.

The maintenance solutions according to the invention can also contain, in the usual amounts, any other ingredients conventionally used in maintenance solutions for contact lenses.

By way of example of another ingredient which can be incorporated into the maintenance solutions according to the invention, mention may be made of germicidal agents such as thimerosal, sorbic acid, 1,5-pentanediol and phenylmercuric salts of alkyl thioethanolamines. Such additional germicidal agents are described in document EP-0 180 309.

Although the description hereinabove refers mainly to decontaminating and cleaning solutions, the compound polyethylene glycol 120 methylglucose dioleate can advantageously be used in other maintenance solutions for contact lenses, such as storage and soaking solutions.

EXAMPLES

An aqueous maintenance solution according to the invention, having the following composition, was prepared:

| | |
|---|---|
| Polyaminopropyl biguanide | 0.001 g |
| (Cosmocil CQ ® 20% solution) | (i.e. 0.0002 g of active principle) |
| Cetrimonium bromide | 0.015 g |
| Hydroxyethyl cellulose | 0.500 g |
| Polyethylene glycol 120 methylglucose dioleate | 1.200 g |
| Poly(oxyethylene)-poly(oxypropylene) block polymer (Poloxamer) | 0.500 g |
| Disodium EDTA | 0.065 g |
| Polyoxyethylene glycol (Macrogol) | 1.200 g |
| Buffer of monosodium phosphate, 2 $H_2O$ and disodium phosphate, 12 $H_2O$ | 2.050 g |
| Sodium chloride | 0.160 g |
| Demineralized water | qs 100 ml |

The above maintenance solution was compared with commercial maintenance solutions. In particular, the humidity-retaining ability of the solutions was determined by working in the following manner.

Dry, hard contact lenses are weighed and are then immersed in each of the test solutions, removed and drained. Each of the lenses is reweighed and the amount of each solution deposited on each lens is deduced therefrom. The solutions deposited are left to evaporate for two hours, the lenses are reweighed and the amount of components remaining on them is determined. The difference between the weight of solution initially deposited on the lenses and the weight of the components remaining on them after two hours of evaporation is an indication of the humidity-retaining ability of the solution.

TABLE I

|  | Example 1 | Commercial maintenance solutions | | |
|---|---|---|---|---|
|  |  | Boston ® Simplicity | Solocare ® Hard | Totalcare ® |
| pH | 7.20 | 7.26 | 7.51 | 7.10 |
| Viscosity-Pa.s × $10^{-3}$ (LVI 30 t/min at 20° C.) | 10 | 31 | 15 | 58 |
| Density | 1.016 | 1.010 | 1.007 | 1.010 |
| Weight of solution remaining on the lens after soaking and draining (g) | 0.0067 | 0.0048 | 0.0042 | 0.0048 |
| Weight of components remaining on the lens after evaporation of the solution (g) | 0.0006 | 0.0002 | 0.0008 | 0.0005 |
| ΔP | 0.0061 | 0.0046 | 0.0034 | 0.0043 |

The results show that the maintenance solution of the example shows a 32.6%, 79.4% and 41.8% improvement in the humidity-retaining ability when compared with commercial solutions.

The ocular tolerance conferred by the various solutions according to the invention, as well as "blank" solutions and solutions according to Examples 6C and 14A of document WO 95/00616 was determined.

Besides the solution of Example 1, the test solutions were as follows:

COMPARATIVE EXAMPLE A

Solution of Example 1 without Glucamate DOE 120.

COMPARATIVE EXAMPLE B

Solution of Example 1 with 0.1% by weight of Glucam® E 20 instead of Glucamate DOE 120.

COMPARATIVE EXAMPLE C

Solution of Example 1 with 1.2% by weight of Glucam® E 20 instead of Glucamate DOE 120.

COMPARATIVE EXAMPLE D

Solution of Example 1 with 3% by weight of Glucam® E 20 instead of Glucamate DOE 120.

COMPARATIVE EXAMPLE E

Solution of Example 6C of document WO 95/00616 (0.3% Glucam® E 20).

EXAMPLE 2

Solution of Example 6C of document WO 95/00616 in which the Glucam® E 20 was replaced by 0.3% by weight of Glucamate DOE 120.

EXAMPLE 3

Solution of Example 6C of document WO 95/00616 in which the Glucam® E 20 was replaced by 1.2% by weight of Glucamate DOE 120.

COMPARATIVE EXAMPLE F

Solution of Example 14A of document wO 95/00616 without Glucam® E 20 (contains a cationic surfactant—Polymer JR—30 M).

COMPARATIVE EXAMPLE G

Solution of Example 14A of document WO 95/00616 with 0.02% by weight of Glucam® E 20.

EXAMPLE 4

Solution of Example 14A of document WO 95/00616 in which the Glucam® E 20 was replaced by 0.02% by weight of Glucamate DOE 120.

The ocular tolerance was determined by direct instillation of the solutions into the eyes of a tester, who was asked if he or she experienced a sensation of eye discomfort.

The results are indicated in Table II below.

TABLE II

| Example No. | Ocular tolerance |
|---|---|
| A | x |
| B | x |
| C | x |
| D | x |
| E | x |
| F | x |
| G | x |
| 1 | o |
| 2 | o |
| 3 | o |
| 4 | o | o no sensation of eye discomfort
x sensation of eye discomfort

The solution of Example 1 was used by 80 contact lens wearers for a period of 180 days, with medical monitoring.

Repeated bimicroscopic observations of the wearers' eyes revealed no manifestation of intolerance to the solution.

Furthermore, the results with regard to the wettability, scratches and protein deposits observed by the investigators on the surface of the lenses show that they are well preserved by the maintenance solution.

Lastly, when asked about the efficacy of maintenance, the comfort when inserting the lenses, the comfort at the end of the day and ease of use of the maintenance solution of Example 1, 96% of the individuals tested said that they were satisfied.

The addition of polyethylene glycol 120 methylglucose dioleate to maintenance solutions for contact lenses, in particular hard contact lenses, leads to solutions which make contact lenses more comfortable to wear by virtue, in particular, of improving the humidity-retaining ability of these solutions on lenses.

The combination of polyethyleneglycol 120 methylglucose dioleate and a nonionic surfactant proves to be particularly advantageous for obtaining a maintenance solution which is better tolerated by users.

What is claimed is:

1. An aqueous solution comprising:
polyethylene glycol 120 methylglucose dioleate of formula:

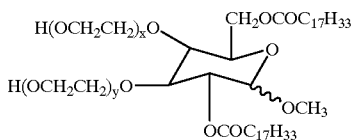

in which x+y=120;
a decontaminating agent selected from the group consisting of chlorhexidine and the water-soluble salts thereof; polyhexamethylene biguanide and the water-soluble salts thereof; quaternary ammonium salts; and mixtures thereof, wherein the decontaminating agent is present in an amount effective to decontaminate a contact lens;
a tonicity agent; and
a buffer.

2. The aqueous solution of claim 1, wherein the concentration of polyethylene glycol 120 methylglucose dioleate is between 0.05 and 5% by weight relative to the total weight of the solution.

3. The aqueous solution of claim 1, wherein the decontaminanting agent comprises a quaternary ammonium salt which is further defined as an alkylammonium halide or an benzalkonium halide.

4. The aqueous solution of claim 1, wherein the buffer is selected from the group consisting of phosphate buffers, borate buffers, and mixtures thereof.

5. The aqueous solution of claim 3, wherein the decontaminating agent is a mixture of polyhexamethylene biguanide or a water-soluble salt thereof and one or more alkylammonium halides, and the buffer is selected from the group consisting of phosphate buffers, borate buffers, and mixtures thereof.

6. The aqueous solution of claim 5, wherein the alkylammonium halide is cetrimonium bromide.

7. The aqueous solution of claim 1, wherein the decontaminating agent represents from $10^{-6}$ to 5% by weight relative to the total weight of the solution.

8. The aqueous solution of claim 7, wherein the decontaminating agent represents from 0.01 to 0.5% by weight relative to the total weight of the solution.

9. The aqueous solution of claim 1, further comprising at least one surfactant chosen from the group consisting of nonionic, cationic and amphoteric surfactants.

10. The aqueous solution of claim 1, further consisting of one or more nonionic surfactants.

11. The aqueous solution of claim 10, wherein the nonionic surfactant is a poly(oxyethylene)-poly(oxypropylene) block polymer.

12. The aqueous solution of claim 9, wherein the surfactant represents 0.01 to 15% by weight relative to the total weight of the composition.

13. The aqueous solution of claim 12, wherein the surfactant represents 0.05 to 1% by weight relative to the total weight of the composition.

14. The aqueous solution of claim 1, further comprising water-soluble cellulose polymer.

15. The aqueous solution of claim 1, further comprising a sequestering agent.

16. The aqueous solution of claim 15, wherein the sequestering agent comprises a compound selected from the group consisting of ethylenediaminetetraacetic acid, gluconic acid, citric acid, tartaric acid, the salts of these acids, and polyphosphate complexes.

17. An aqueous solution comprising:
polyethylene glycol 120 methylglucose dioleate of formula:

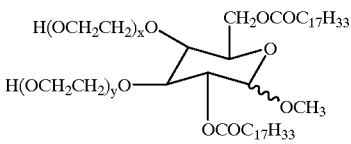

in which x+y=120;
a decontaminating agent selected from the group consisting of chlorhexidine and the water-soluble salts thereof; polyhexamethylene biguanide and the water-soluble salts thereof; quaternary ammonium salts; and mixtures thereof, wherein the decontaminating agent is present in an amount effective to decontaminate a contact lens;
a surfactant;
a sequestering agent;
a tonicity agent; and
a buffer.

18. The aqueous solution of claim 17, wherein the concentration of polyethylene glycol 120 methylglucose dioleate is between 0.05 and 5% by weight relative to the total weight of the solution.

19. The aqueous solution of claim 17, wherein the decontaminating agent is a mixture of polyhexamethylene biguanide or water-soluble salt thereof and one or more alkylammonium halides.

20. The aqueous solution of claim 19, wherein the alkylammonium halide is cetrimonium bromide.

21. The aqueous solution of claim 17, wherein the decontaminating agent represents from $10^{-6}$ to 5% by weight relative to the total weight of the solution.

22. The aqueous solution of claim 21, wherein the decontaminating agent represents from 0.01 to 0.5% by weight relative to the total weight of the solution.

23. The aqueous solution of claim 17, wherein the surfactant is selected from the group consisting of nonionic, cationic and amphoteric surfactants.

24. The aqueous solution of claim 23, wherein the surfactant consists of one or more nonionic surfactants.

25. The aqueous solution of claim 24, wherein the nonionic surfactant is a poly(oxyethylene)-poly(oxypropylene) block polymer.

26. The aqueous solution of claim 17, wherein the surfactant represents 0.01 to 15% by weight relative to the total weight of the composition.

27. The aqueous solution of claim 26, wherein the surfactant represents 0.05 to 1% by weight relative to the total weight of the composition.

28. The aqueous solution of claim 17, further comprising water-soluble cellulose polymer.

29. The aqueous solution of claim 17, wherein the sequestering agent comprises a compound selected from the group consisting of ethylenediaminetetraacetic acid, gluconic acid, citric acid, tartaric acid, the salts of these acids, and polyphosphate complexes.

30. The aqueous solution of claim 17, wherein the buffer is selected from the group consisting of phosphate buffers, borate buffers and mixtures thereof.

31. The aqueous solution of claim 17, wherein the decontaminanting agent comprises a quaternary ammonium salt which is further defined as an alkylammonium halide or an benzalkonium halide.

32. An aqueous solution comprising:
polyethylene glycol 120 methylglucose dioleate of formula:

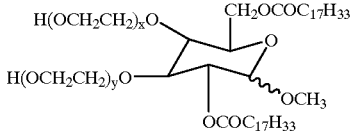

in which x+y=120;
a decontaminating agent, wherein the decontaminating agent is present in an amount effective to decontaminate a contact lens;
a sequestering agent;
a tonicity agent; and
a buffer.

33. The aqueous solution of claim 32, wherein the decontaminating agent is selected from the group consisting of chlorhexidine and the water-soluble salts thereof; polyhexamethylene biguanide and the water-soluble salts thereof; quaternary ammonium salts; and mixtures thereof.

34. The aqueous solution of claim 32, wherein the decontaminating agent is a mixture of polyhexamethylene biguanide or a water-soluble salt thereof and one or more alkylammonium halides.

35. The aqueous solution of claim 34, wherein the alkylammonium halide is cetrimonium bromide.

36. The aqueous solution of claim 32, wherein the decontaminating agent represents from $10^{-6}$ to 5% by weight relative to the total weight of the solution.

37. The aqueous solution of claim 33, wherein the decontaminating agent represents from 0.01 to 0.5% by weight relative to the total weight of the solution.

38. The aqueous solution of claim 32, further comprising at least one surfactant chosen from the group consisting of nonionic, cationic and amphoteric surfactants.

39. The aqueous solution of claim 38, wherein the surfactant consists of one or more nonionic surfactants.

40. The aqueous solution of claim 39, wherein the nonionic surfactant is a poly(oxyethylene)-poly(oxypropylene) block polymer.

41. The aqueous solution of claim 38, wherein the surfactant represents 0.01 to 15% by weight relative to the total weight of the composition.

42. The aqueous solution of claim 38, wherein the surfactant represents 0.05 to 1% by weight relative to the total weight of the composition.

43. The aqueous solution of claim 30, further comprising water-soluble cellulose polymer.

44. The aqueous solution of claim 32, wherein the sequestering agent comprises a compound selected from the group consisting of ethylenediaminetetraacetic acid, gluconic acid, citric acid, tartaric acid, the salts of these acids, and polyphosphate complexes.

45. The aqueous solution of claim 32, wherein the buffer is selected from the group consisting of phosphate buffers, borate buffers, and mixtures thereof.

46. The aqueous solution of claim 33, wherein the decontaminanting agent comprises a quaternary ammonium salt which is further defined as an alkylammonium halide or an benzalkonium halide.

47. An aqueous solution comprising;
polyethylene glycol 120 methylglucose dioleate of formula;

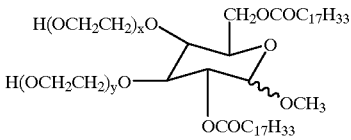

in which x+y=120;
a decontaminating agent comprising a mixture of polyhexamethylene biguanide or a water-soluble salt thereof and one or more alkylammonium halides, wherein the decontaminating agent is present in an amount effective to decontaminate a contact lens;
a tonicity agent; and
a buffer.

48. The aqueous solution of claim 47, wherein the concentration of polyethylene glycol 120 methylglucose dioleate is between 0.05 and 5% by weight relative to the total weight of the solution.

49. The aqueous solution of claim 49, wherein the alkylammonium halide is cetrimonium bromide.

50. The aqueous solution of claim 49, wherein the decontaminating agent represents from $10^{-6}$ to 5% by weight relative to the total weight of the solution.

51. The aqueous solution of claim 50, wherein the decontaminating agent represents from 0.01 to 0.5% by weight relative to the total weight of the solution.

52. The aqueous solution of claim 47, further comprising at least one surfactant chosen from the group consisting of nonionic, cationic and amphoteric surfactants.

53. The aqueous solution of claim 52, wherein the surfactant consists of one or more nonionic surfactants.

54. The aqueous solution of claim 53, wherein the nonionic surfactant is a poly(oxyethylene)-poly(oxypropylene) block polymer.

55. The aqueous solution of claim 52, wherein the surfactant represents 0.01 to 15% by weight relative to the total weight of the composition.

56. The aqueous solution of claim 55, wherein the surfactant represents 0.05 to 1% by weight relative to the total weight of the composition.

57. The aqueous solution of claim 47, further comprising water-soluble cellulose polymer.

58. The aqueous solution of claim 47, further comprising a sequestering agent.

59. The aqueous solution of claim 50, wherein the sequestering agent comprises a compound selected from the group consisting of ethylenediaminetetraacetic acid, gluconic acid, citric acid, tartaric acid, the salts of these acids, and polyphosphate complexes.

60. The aqueous solution of claim 47, wherein the buffer is selected from the group consisting of phosphate buffers, borate buffers, and mixtures thereof.

* * * * *

UNITED STATES PATENT AND TRADEMARK OFFICE
CERTIFICATE OF CORRECTION

PATENT NO. : 6,207,628 B1
DATED : March 27, 2001
INVENTOR(S) : Patrice Soyer and Arila Pochet It is certified that error appears in the above-identified patent and that said Letters Patent is hereby corrected as shown below:

Column 8, claim 31,
Line 67, please delete "decontaminanting" and insert -- decontaminating -- therefor.

Signed and Sealed this

Thirteenth Day of November, 2001

*Attest:*

*Attesting Officer*

NICHOLAS P. GODICI
*Acting Director of the United States Patent and Trademark Office*